(12) United States Patent
Vila et al.

(10) Patent No.: US 11,737,695 B2
(45) Date of Patent: Aug. 29, 2023

(54) METHOD FOR DETERMINING A MEMBERSHIP FUNCTION, INTENDED TO BE APPLIED TO ESTIMATE A STRESSED STATE OF A PERSON

(71) Applicants: Commissariat à l'Energie Atomique et aux Energies Alternatives, Paris (FR); UNIVERSITE GRENOBLE ALPES, Saint Martin d'Heres (FR)

(72) Inventors: Gaël Vila, Grenoble (FR); Christelle Godin, Grenoble (FR); Aurélie Campagne, Fontaine (FR); Sylvie Charbonnier, Echirolles (FR)

(73) Assignees: Commissariat à l'Energie Atomique et aux Energies Alternatives, Paris (FR); UNIVERSITE GRENOBLE ALPES, Saint Martin d'Heres (FR)

( * ) Notice: Subject to any disclaimer, the term of this patent is extended or adjusted under 35 U.S.C. 154(b) by 205 days.

(21) Appl. No.: 17/132,913

(22) Filed: Dec. 23, 2020

(65) Prior Publication Data
US 2021/0196172 A1 Jul. 1, 2021

(30) Foreign Application Priority Data
Dec. 26, 2019 (FR) ..................................... 19 15596

(51) Int. Cl.
*A61B 5/00* (2006.01)
*A61B 5/16* (2006.01)

(52) U.S. Cl.
CPC ............ *A61B 5/165* (2013.01); *A61B 5/6801* (2013.01); *A61B 5/7264* (2013.01);
(Continued)

(58) Field of Classification Search
CPC ..... A61B 5/165; A61B 5/6801; A61B 5/7264; A61B 5/7267; A61B 5/7282; A61B 5/4884; A61B 5/681; A61B 5/6824
See application file for complete search history.

(56) References Cited

U.S. PATENT DOCUMENTS

2020/0015729 A1\* 1/2020 Vila ........................ A61B 5/165

FOREIGN PATENT DOCUMENTS

EP 3 305 186 A1 4/2018

OTHER PUBLICATIONS

Charbonnier, S. et al., "A Multi-feature Fuzzy Index to Assess Stress Level from Bio-signals," 2018 40th Annual International Conference of the IEEE Engineering in Medicine and Biology Society, EMBC, IEEE, July 18, 2018, XP 033431946, 4 pages.
(Continued)

*Primary Examiner* — Eugene T Wu
(74) *Attorney, Agent, or Firm* — Oblon, McClelland, Maier & Neustadt, L.L.P.

(57) ABSTRACT

A method for determining a membership function, the membership functions allowing a stress level of a user to be determined on the basis of a physiological parameter measured on the user, the membership function varying, depending on the physiological parameter, between:
  a first value, representative of a rest state;
  and a second value, representative of a stressed state;
the membership function taking into account a distribution function, which is defined beforehand, the distribution function being a continuous and monotonic function, the distribution function being applied to a normalized parameter established on the basis of a measured physiological parameter, the method comprising determining a normalization function, and optionally a standardization function, the normalization function and the optional standardization
(Continued)

function being determined on the basis of physiological parameters measured on a plurality of test individuals, in various calibration periods.

17 Claims, 7 Drawing Sheets

(52) U.S. Cl.
CPC .......... *A61B 5/7267* (2013.01); *A61B 5/7282* (2013.01); *A61B 5/4884* (2013.01)

(56) References Cited

OTHER PUBLICATIONS

French Preliminary Search Report dated Dec. 7, 2020 in French Application 19 15596 filed Dec. 26, 2019 (with English Translation of Categories of Cited Documents and Written Opinion), 10 pages.

* cited by examiner

MMETHOD FOR DETERMINING A
MEMBERSHIP FUNCTION, INTENDED TO
BE APPLIED TO ESTIMATE A STRESSED
STATE OF A PERSON

TECHNICAL FIELD

The technical field of the invention is the determination of a stress level of a user on the basis of at least one measurement of a physiological parameter performed on the user. The stress level is determined by implementing a membership function, stemming from fuzzy logic.

TECHNICAL FIELD

It is possible to determine a stress level of an individual on the basis of measurements of one or more physiological parameters of said individual. The physiological parameter may be a cardiac activity, for example measured via an electrocardiogram (ECG) or a simple determination of a cardiac frequency, or a muscular activity, measured via an electromyogram (EMG), or even a measurement of the electrical conductance of the skin. The publication Ollander "A comparison of wearable and stationary sensors for stress detection", 2016 IEEE international conference on Systems, Man and Cybernetics (SMC), October 2016, describes how certain physiological parameters may be used to establish a stress indicator for an individual. The emergence of portable connected sensors intended to be worn by an individual has made it possible to take measurements of physiological parameters both simply and inexpensively. It is for example a question of specific sensors able to be fastened to a bracelet or integrated into watches or connected to smart phones. For example, the device Empatica E4 comprises various sensors allowing physiological parameters such as electrodermal activity, cardiac activity or temperature to be easily accessed. On the basis of the measured parameters, classification algorithms may be implemented, so as to determine whether the individual is in a stressed state or in a rest state. Certain classification algorithms are based on fuzzy logic. This type of algorithm is for example described in the publication Kumar M "Fuzzy techniques for subjective workload-score modeling under uncertainties", IEEE transactions on systems, man and cybernetics—part B, Vol. 38, No. 6, December 2008. This type of algorithm requires a learning phase to be carried out, in which an individual is placed in a stressful situation, or in various stressful situations.

The publication De Santos Sierra A. et al. "Real-time stress detection by means of physiological signals", Recent Application in Biometrics (2011 Jul. 27) describes an analogous approach, according to which, during training, the unit user must be successively in a stressed state and in a rest state. The fact that training, during which the user is placed in a stressful situation, is required is constraining. In addition, the reliability of such methods may be compromised by physiological variability from one user to the next.

Patent application US20200015729, describes a method allowing a stress level of a user to be determined on the basis of physiological parameters measured on the user. One advantageous aspect of this method is that it does not require the user to be placed in a stressed state during the calibration. In other words, the calibration is performed only when the user is at rest. This allows a particularly simple implementation of the method, using measuring equipment worn by the user. In addition, the calibration may be renewed periodically. In this patent application, the stress level of the user is determined using the principles of fuzzy logic: a membership function is established beforehand. The stress level is determined depending on the image, generated by the membership function, of the value of the measured physiological parameter. This method is also described in the publication Charbonnier, Sylvie et al. "A Multi-feature Fuzzy Index to Assess Stress Level from Bio-signals. Conference proceedings: Annual International Conference of the IEEE Engineering in Medicine and Biology Society". IEEE Engineering in Medicine and Biology Society. Conference. 2018. 1086-1089.

The inventors believe that the method described in patent application US20200015729, and in the aforementioned publication, could be improved, so as to increase the sensitivity and the specificity of the detection of a stress level. This is the objective of the method described below.

SUMMARY OF THE INVENTION

A first subject of the invention is a method for determining a membership function, the membership functions allowing a stress level of a user to be determined on the basis of a physiological parameter measured on the user, during a measurement period, the membership function varying, depending on the physiological parameter, between:
  a first value, representative of a rest state;
  and a second value, representative of a stressed state;
the membership function taking into account a distribution function, which is defined beforehand, the distribution function being a continuous and monotonic function, the distribution function being applied to a normalized parameter that is established on the basis of a measured physiological parameter, the method comprising:
a) measuring values of a physiological parameter, in various calibration periods, on at least one test individual, each test individual being placed, in each calibration period, either in a rest state, or in a stressed state, or in an intermediate state, the intermediate state being a state in which the test individual is considered to be neither in a stressed state, nor in a rest state;
b) optionally, applying a standardization function to the values measured at rest, in step a), to obtain standardized parameters, the standardization function being concave;
c) on the basis:
  of the values measured in a) and/or optionally standardized in b);
  of the distribution function;
determining a normalization function, the normalization function being intended to be applied to the measured, and optionally standardized, values of the physiological parameter, in order to establish normalized values, the determination of the normalization function comprising:
  an optimization of a rest interval, representative of the values of the parameters measured when each test individual is at rest;
  an optimization of a threshold distance, between the rest interval, and a stressed interval, representative of the values of the parameter measured when each test individual is in a stressed state;
d) determining the membership function associated with the physiological parameter, the membership function corresponding to a composition of the distribution function, of the normalization function and of the optional standardization function.

The role of the normalization function is to distribute the measured values of the physiological parameters, which are optionally standardized, optimally so as to optimize, after application of the distribution function, the estimation of the stress level of the individual.

In a), the values of the physiological parameter that are measured while each test individual is in a stressed, rest or intermediate state may be grouped into a stressed class, a rest class and an intermediate class, respectively, so that, in step c), the rest interval is optimized so as to optimize a classification, by the distribution function, of normalized values corresponding to the rest class and to a union of the intermediate class and of the stressed class, respectively;

the threshold distance is optimized so as to optimize a classification, by the distribution function of normalized values corresponding to the stressed class and to a union of the intermediate class and of the rest class, respectively.

Step c) may comprise determining:
an indicator of classification of the normalized values between the rest class and a union of the intermediate class and of the stressed class, the classification indicator being based on a proportion of false positives and of false negatives;
an indicator of classification of the normalized values between the stressed class and a union of the intermediate class and of the rest class, the classification indicator being based on a proportion of false positives and of false negatives Step c may comprise
determining an optimal rest interval, by setting the threshold distance;
then determining the optimal threshold distance, depending on the optimal rest interval.

Step c) may comprise optimizing an extent of the rest interval.

Step c) may comprise optimizing a scale factor, the threshold distance being determined by multiplying the scale factor by the extent of the rest interval.

The normalization function may be an affine function; c) may comprise determining parameters of the affine function on the basis of the optimized rest interval and of the optimized threshold distance.

The standardization function may be of logarithmic or square-root type.

The method may comprise:
following a), computing a coefficient of asymmetry of a distribution of the values of the physiological parameter that are measured when each test individual is at rest, the coefficient of asymmetry quantifying the asymmetry of the distribution;
comparing the coefficient of asymmetry to a predefined threshold;
depending on the comparison, implementing b).

According to an embodiment:
steps a) to d) form a sequence of steps that is associated with the physiological parameter measured in a), and leading to the determination of a membership function associated with the physiological parameter;
the method further comprises various sequences of steps a) to d), respectively associated with various physiological parameters, so as to determine various membership functions, each membership function being respectively associated with one physiological parameter.

A second subject of the invention is determining a stress level of a user, depending on a physiological parameter measured on the user, during a measurement period, the value of which is liable to vary depending on the stress level of the user, the method comprising:
i) measuring a value of the physiological parameter during a measurement period;
ii) applying a membership function to the value of the physiological parameter measured in step i);
iii) estimating the stress level of the user depending on the value of the membership function computed in step ii);
wherein the membership function is a function determined using the method according to the first embodiment.

A third subject of the invention is a method for determining a stress level of a user, depending on a plurality of physiological parameters of the user, the value of each physiological parameter being liable to vary depending on the stress level of the user, the method comprising:
i) measuring values of various physiological parameters during a measurement period;
ii) for each value of the physiological parameter measured in i), applying a membership function associated with the physiological parameter;
iii) estimating the stress level by combining the values of the membership functions computed in step i);
wherein at least one membership function, associated with one physiological parameter, is a function determined using the method according to the first embodiment.

The method according to the second or third subject of the invention may comprise an initialization phase, containing various initialization periods, in which periods the user is considered to be in a rest state, the initialization phase comprising:
measuring, in each initialization period, one physiological parameter;
determining an indicator of the dispersion of the values measured in each initialization period;
the method comprising, prior to steps i) to iii), adjusting the membership function established for the physiological parameter so as to take into account the dispersion indicator.

The invention will be better understood on reading the description of the exemplary embodiments, which are described, in the rest of the description, with reference to the figures listed below.

DESCRIPTION OF PARTICULAR EMBODIMENTS

Figure 1:
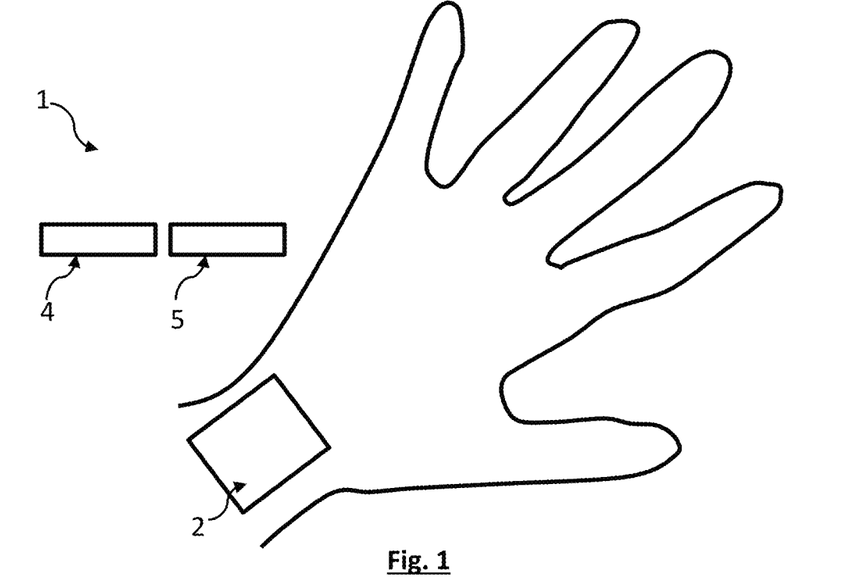
FIG. 1 shows a device allowing the invention to be implemented.

FIG. 1 shows a device 1 allowing the invention to be implemented. A sensor 2 is placed against the body of an individual, for example on his wrist. The sensor 2 is configured to measure the value x(t) of a physiological parameter of the individual during a measurement period t. The term period designates a time interval, for example a few seconds or a few minutes. The value of the physiological parameter in question may vary depending on a stress level of the individual. The physiological parameter x may be a parameter such as described in the publications cited with respect to the prior art, in which it is designated by the term "feature". The physiological parameter may for example be:

A parameter related to a cardiac activity of the individual, for example cardiac frequency. Such a parameter may be measured by electrodes similar to the electrodes of an electrocardiogram (ECG), or by optical means, of the photoplethysmography (PPG) type.

It may also be a question of a mean of the cardiac frequency or of a dispersion parameter of the cardiac frequency such as its standard deviation, calculated during a preset time period. The physiological parameter may result from a frequency analysis of the cardiac activity such as an analysis of the inter-beat interval (IBI). In an ECG, this interval may lie between two R peaks of two consecutive cardiac pulses. The frequency analysis may be carried out in frequency ranges comprised between 0 Hz and 0.5 Hz, and more specifically, for example between 0 and 0.003 Hz (ultra-low frequencies), or between 0.003 and 0.04 Hz (very low frequencies), between 0.04 Hz and 0.15 Hz (low frequencies), or between 0.15 Hz and 0.5 Hz (high frequencies).

A parameter related to a muscular activity of the individual, this type of parameter being able to be measured by electromyography (EMG).

A parameter related to the electrodermal activity of the individual, representative of electrical-conduction or electrical-impedance properties of the skin (for example electrodermal impedance or conductance) and/or capacitive properties of the skin. It may be a question of a mean value of the conductance of the skin or of the mean absolute value of a derivative of the conductance of the skin. It may also be a question of a frequency, or of a mean duration or of a mean amplitude of electrodermal responses calculated during a preset time period. More generally, the parameter in question is a feature of an electrodermal response.

A skin temperature of the individual.

A measurement of a movement, for example an acceleration along at least one axis, such a measurement allowing a tremble or a physical activity liable to impact the physiology of the individual to be measured. The parameter in question may be a norm of the acceleration.

A measurement of a cortical activity, for example taken using electroencephalography (EEG) electrodes. It may for example be a question of a spectral power in a preset frequency band, calculated in a preset time period.

The physiological parameter may be a parameter representing the cardiac frequency (or heart rate). If $HR_j$ is the heart rate measured at a time j, the physiological parameter x(t) at t may be:

$$x(t) = \sqrt{\frac{1}{N_j} \sum_j (HR_j - HR_{j-1})^2}$$

where $N_j$ is a number of heart rate measurements taken into account, and $t-N_j \leq j \leq t$. The number $N_j$ is set so as to include the measurements of the hear rate during a sliding duration of a few seconds or a few tens of seconds, of a few minutes, for example 60 seconds.

If $IBI_j$ is the inter-beat interval measured at a time j, the physiological parameter x(t) at t may be:

$$x(t) = \sqrt{\frac{1}{N_j} \sum_j (IBI_j - IBI_{j-1})^2}$$

where $N_j$ is a number of inter-beat intervals taken into account, and $t-N_j \leq j \leq t$. The number $N_j$ is set so as to include the measurements of the inter-beat interval during a sliding duration of a few seconds or a few tens of seconds, of a few minutes, for example 60 seconds.

The physiological parameters described in the two preceding paragraphs are particularly suitable for an implementation of the invention. They may be used alone or be combined, as described below. A physiological parameter is determined, for a measurement period, on the basis of signals measured during the measurement period. It may result from a statistical or frequency analysis of these signals.

The objective of the invention is to determine a stress level Sl(t) of a user in various measurement periods t. The user is a living individual, for example a human being or an animal.

The sensor 2 is connected to a microprocessor 4, the latter being connected to a memory 5 in which are stored instructions for implementing the method described below. The microprocessor 4 receives the measurements from the sensor 2, via a wired link or a wireless link. The microprocessor 4 may be borne by the user, it being placed nearby the sensor or incorporated into an associated device borne by the user, a nomadic object such as a smart phone for example. The microprocessor 4 may also be remote from the user.

The operation of the device 1 is described in patent application US20200015729, and more particularly in steps 130 and 140 and FIG. 3 of said patent application. Generally, the device implements a method that is repeated in various measurement periods t. The objective is to estimate a stress level Sl(t) corresponding to each measurement period. In each period, a physiological parameter x(t), such as defined above, is determined. The method comprises applying a membership function $f$, such that the stress level Sl(t), during the measurement period, corresponds to the image, generated by the membership function, of the physiological parameter. In other words, $$Sl(t)=f(x(t))$$

The membership function $f$ is intended to estimate a stress level Sl on the basis of the value of a physiological parameter x(t) measured in a measurement period t. The stress level Sl may for example vary between 0 and 1, 0 corresponding to a rest state and 1 corresponding to a stressed state of the user. According to the principles of fuzzy logic, the membership function $f$ may define intermediate levels, comprised between 0 and 1, and corresponding to a state in which the user is neither in a stressed state, nor at rest. The membership function $f$ is preferably continuous in an input space E defined by the values capable of being taken by the measured physiological parameter. The input space E may for example be the set of all real positive numbers. Thus, $f: E = \mathbb{R}^+ \to [0,1]$ and $f(x(t))=Sl(t)$. The membership function $f$ may for example be piecewise linear, or take the form of a hyperbolic tangent or sigmoid.

Figure 2:
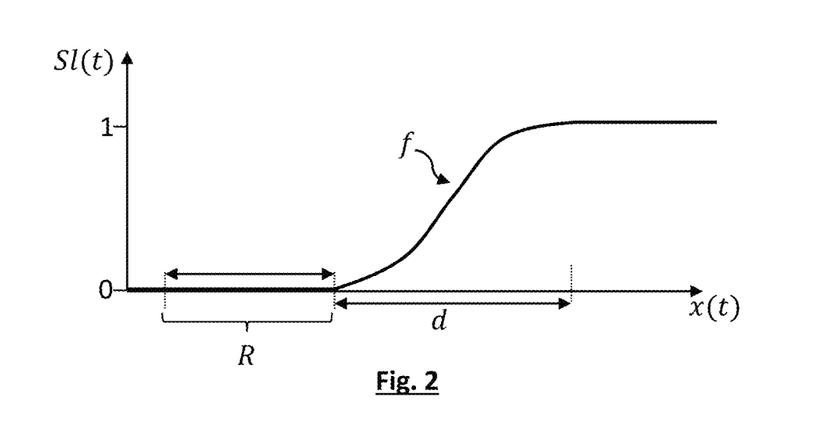
FIG. 2 illustrates the main steps of one embodiment of the invention.

FIG. 2 shows an example in which the membership function $f$ is of sigmoid type. A sigmoid function is of type:

$$f(x) = \frac{1}{1+e^x} \quad (3)$$

When the values of the parameter x(t) are comprised in a rest interval $X_r$, the stress level Sl(t) is close to 0 or equal to 0. The user is considered to be at rest. When the values of the parameter x(t) are distant, by a distance smaller than a threshold distance d, from the rest interval R, the user is considered to be in an intermediate state, between the rest state and a stressed state: 0<Sl(t)<1. When the values of the parameter x(t) are distant, by a distance larger than a threshold distance d, from the rest interval, the user is considered to be in a stressed state. Sl(t) is then equal to 1 or close to 1.

The example given with reference to FIG. 2 is valid when the membership function $f$ is increasing, i.e. the stress level increases as the measured value of the physiological parameter increases. In certain particular cases, for example when the parameter in question is the resistance of the skin, the membership function $f$ is decreasing: the stress level increases as the value of the measured parameter decreases.

According to one possibility, the method described above may be applied by measuring, in each measurement period t, various physiological parameters $x_i$, the index i identifying the parameter in question, with $1 \leq i \leq I$, I designating the number of physiological parameters in question. One membership function $f_i$ is then defined for each physiological parameter $x_i$. The membership functions $f_i$, $f_{i+1}$ respectively associated with two different parameters $x_i$, $x_{i+1}$ may be established independently of each other. It is however preferable, for each membership function, that the rest state and the stressed state respectively correspond to the same levels, for example 0 for the rest state and 1 for the stressed state. A definition of I membership functions $f_1 \ldots f_I$, respectively associated with the I measured physiological parameters $x_1 \ldots x_I$, is thus obtained.

After each membership function $f_i$ has been defined, the method comprises, in each measurement period t, implementing it, for each measured parameter $x_i(t)$, so as to determine a stress level $Sl_i(t)$ associated with each parameter $x_i(t)$, using the expression $Sl_i(t)=f_i(x_i(t))$. A definition of I stress levels $Sl_1(t) \ldots Sl_I(t)$, respectively associated with the I physiological parameters $x_1 \ldots x_I$ in question, is thus obtained. The various stress levels $Sl_1(t) \ldots Sl_I(t)$, respectively associated with each parameter $x_i(t)$, are combined, so as to determine an overall, or multiparameter, stress level Sl(t), according to the principles of fuzzy logic. The combination may be a computation of a mean value or of a median value. It may also be a question of a weighted mean, in which each stress level $Sl_i(t)$ is assigned a weighting factor $\lambda_i$ depending on the importance that it is desired to attribute to the physiological parameter $x_i$ relative to the other parameters in question. The various stress levels $Sl_1(t) \ldots Sl_I(t)$ may be combined by applying predefined inference rules. On the basis of the multiparameter stress level Sl(t), it is possible to determine whether the user is in a stressed state.

The inventors have considered it necessary for the membership function to be refined, so as to process the measured values of each physiological parameter. This is particularly relevant when various physiological parameters $x_i$ are addressed in each measurement period t, so as to obtain a multiparameter stress level. The objective of the processing is to improve the performance of the determination of the stress level, and notably sensitivity (i.e. a minimum proportion of false negatives) and specificity (i.e. a minimum proportion of false positives).

The processing of the measured values consists in applying a membership function to the value of a physiological parameter measured in each measurement period. The invention differs from the prior art in that the membership function is a composition of various functions, defined in a calibration phase that is described below. More precisely, for each physiological parameter $x_i$ in question, a membership function $f_i$ is defined in the calibration phase. Each membership function $f_i$ associated with one physiological parameter $x_i$ corresponds to a composition:

optionally of a standardization function $T_i$. The standardization function is generally determined in the calibration phase. The standardization function is defined such that when a user is at rest, the values $x_i(t)$ of the physiological parameter $x_i$ are distributed in a distribution that approaches a symmetric distribution, a Gaussian distribution for example. The application of the standardization function to a measured value $x_i(t)$ of the physiological parameter $x_i$ leads to the obtainment of a standardized value $T_i(x_i(t))$. When the method is based on a measurement of various physiological parameters $x_1$, $x_2$ during a measurement period t, the standardization functions $T_1$, $T_2$ respectively associated with the parameters $x_1$, $x_2$, are generally different.

a normalization function $A_i$, established during the calibration phase. The normalization function $A_i$ allows the measured values $x_i(t)$ of the physiological parameter, or of the standardized values $T_i(x_i(t))$, to be distributed optimally with respect to specificity and sensitivity. The application of the normalization function $A_i$ to a measured value $x_i(t)$ of the physiological parameter $x_i$, or to a standardized value $T_i(x_i(t))$, allows a normalized value $A_i(x_i(t))$ or $A_i(T_i(x_i(t)))$ to be obtained. When the method is based on a measurement of various physiological parameters $x_1$, $x_2$ during a measurement period t, the normalization functions $A_1$, $A_2$ respectively associated with the parameters $x_1$, $x_2$, are generally different.

a predefined distribution function $S_i$. The distribution function $S_i$, applied to a normalized value $A_i(x_i(t))$ or $A_i$ $(T_i(x_i(t)))$, allows a stress level $Sl_i(t)$ associated with the physiological parameter $x_i$ to be estimated. The distribution function is preferably monotonic, and preferably continuous. The distribution function $S_i$ may for example be piecewise linear, or take the form of a hyperbolic tangent or sigmoid. When the method is based on a measurement of various physiological parameters $x_1$, $x_2$ during a measurement period t, the distribution functions $S_1$, $S_2$ respectively associated with the parameters $x_1$, $x_2$, may be different or identical.

Thus, the method implements, for each physiological parameter $x_i$ in question, a membership function $f_i$ formed by a composition of the optional standardization function $T_i$, with the normalization function $A_i$ and the distribution function $S_i$. Thus, $$f_i = S_i \circ A_i \circ T_i \tag{4}$$

or $$f_i = S_i \circ A_i \tag{5}$$

∘ designating the function-composition operator.

The normalization function $A_i$ allows, for a given user, the measured physiological parameters to be projected into a space comprising the antecedents of the distribution function. The normalization function $A_i$ is optimized so as to optimize, after the distribution function $S_i$ has been applied, the estimation of the stress level in particular with respect to specificity and sensitivity.

Figure 3A:
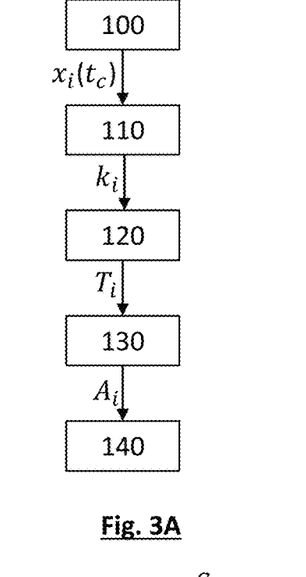
FIG. 3A schematically shows the main steps of a calibration phase, allowing the membership function to be determined.

The main steps of the calibration phase, allowing the standardization and normalization functions to be defined taking into account a predefined distribution function, will now be described with reference to FIG. 3A. The calibration phase is performed on a test population, formed from at least one test individual, and preferably from a plurality of test individuals. In this phase, each test individual of the test population follows a protocol, so as to be able to be considered to be either in a rest state, or in a stressed state, or in an intermediate state, i.e. neither in a rest state nor a stressed state. The intermediate state may for example correspond to a state in which the test individual is active, without being stressed: he is for example performing a physical and/or intellectual activity that is not considered to be stressful. Each test individual is considered to be representative of the user intended to use the device. Protocols known to those skilled in the art allow an individual to be considered to be in a stressed state. It is for example a protocol usually designated by the acronym "MST" (Mental Stress Test), in which an individual must count backwards in increments starting from a preset number. The individual is filmed, and the trial is carried out in the presence of two observers. For example, the individual must count backwards from 1022 in increments of 13. It may also be a question of a protocol usually designated by the acronym "TSST" (Trier Social Stress Test), in which the individual is filmed during a mock recruitment interview in front of two observers. In each protocol, one or more physiological parameters are measured, during various periods. During the calibration phase, the periods $t_c$ in which physiological parameters are measured are called calibration periods.

Steps 100 to 140 described below relate to one physiological parameter $x_i$. When the method implements various physiological parameters, steps 100 to 140 are performed in parallel, for each addressed physiological parameter.

Step 100: measuring values $x_i(t_c)$ of the physiological parameter $x_i$ during a plurality of calibration periods $t_c$, and for one or more test individuals. The measurements are taken while each test individual is in a state considered to be known. The population and number of measurements are dimensioned so as to obtain a sample that is statistically representative of each parameter, and in each state (stress state, rest state, intermediate state). Typically, at least 30 measured values are obtained for each parameter and in each state.

Step 110: Study of the symmetry of the values measured in step 100, while each test individual is at rest.

For the physiological parameter $x_i$, a distribution $D_i$ of the values $x_i(t_c)$, measured while each test individual is at rest, is determined. A coefficient of symmetry $k_i$ is computed for the physiological parameters. The coefficient of symmetry $k_i$ quantifies the symmetry of the distribution $D_i$. For example, the coefficient of symmetry $k_i$ is such that:

$$k_i = \frac{E[x_i(t_c) - \mu_i]^3}{\sigma_i^3} \tag{6}$$

where $\mu_i$ and $\sigma_i$ are the mean and standard deviation of the distribution $D_i$, respectively. E is the expectation operator. When $k_i$ is positive, the distribution $D_i$ is centered on the lowest values of the parameter $x_i$. When $k_i$ is negative, the distribution $D_i$ is centered on the highest values of the physiological parameter $x_i$. The lower the absolute value of $k_i$, the more the distribution $D_i$ is considered to be symmetric.

Following step 110, a coefficient of symmetry $k_i$ corresponding to the distribution $D_i$ of the values $x_i(t_c)$ of the physiological parameter $x_i$ that were measured in the calibration phase, when each test individual is at rest, is obtained.

Step 120: Determining a Standardization Function

This step is optional. It is preferably implemented when, following step 110, the absolute value $|k_i|$ of the coefficient of symmetry $k_i$ of a distribution $D_i$ exceeds a certain threshold $k_{th}$: the distribution $D_i$ is then considered to be asymmetric. A standardization function $T_i$ is applied to each value $x_i(t_c)$, such that the distribution $D'_i$ of the data $T_i(x_i(t_c))$, obtained following the application of the standardization function, has a coefficient of symmetry $k'_i$ the absolute value of which is lower than the absolute value of $k_i$: $|k'_i| < |k_i|$. Preferably, $|k'_i| < k_{th}$, such that the distribution $D'_i$ is considered to be symmetric.

The standardization function $T_i$ is preferably a concave function. It may for example be a logarithmic function, for example a function that is logarithmic to the base 10, or a square-root function. Whatever the (logarithmic, square-root or other) type of standardization function in question, the standardization function is parameterized to minimize the absolute value of the coefficient of symmetry of the distribution $D'_i$. Thus, $$T_i = \underset{T_i}{\mathrm{argmin}}(|k'_i|) \tag{7}$$

Figure 4A:
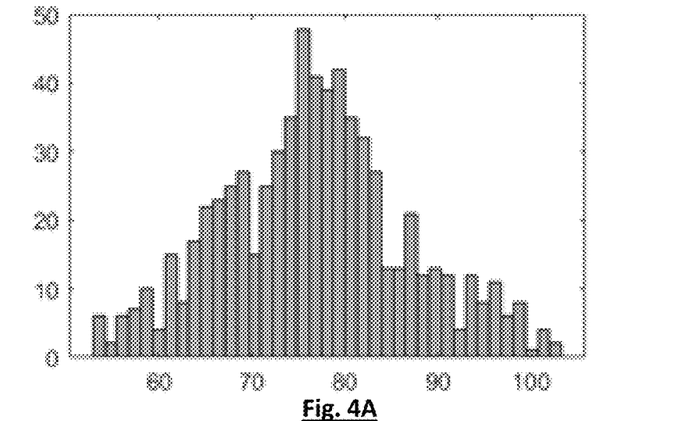
FIG. 4A shows a distribution, considered to be symmetric, of values of one physiological parameter measured in a calibration phase, while each test individual is at rest.

FIG. 4A shows an experimentally obtained statistical distribution of a mean value of the heart rate of 20 test individuals in rest state. The coefficient of symmetry of such a distribution is close to 0.

Figure 4B:
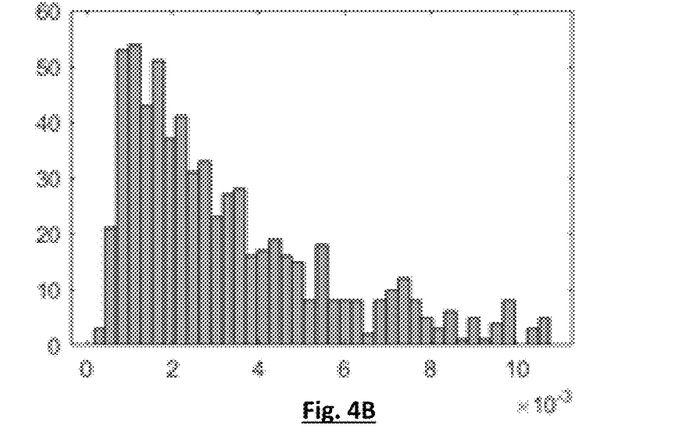
FIG. 4B shows a distribution, considered to be asymmetric, of values of another physiological parameter measured in a calibration phase, while each test individual is at rest.
Figure 4C:
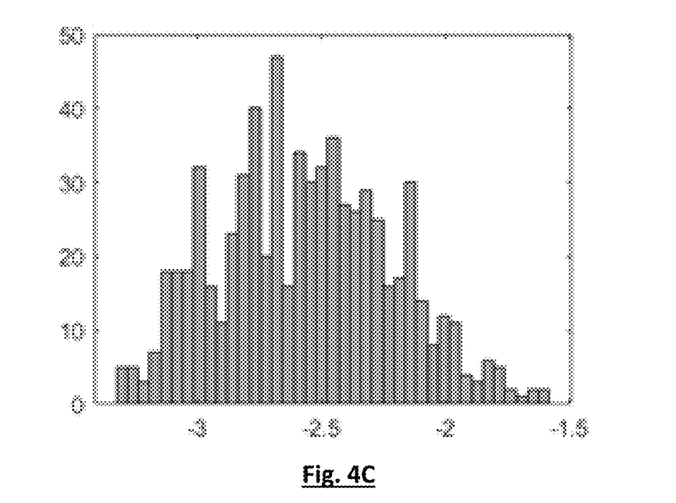
FIG. 4C shows a distribution obtained after a standardization function has been applied to the values, the distribution of which is shown in FIG. 4B. Comparison of FIGS. 4B and 4C illustrates the effect of the standardization function.

FIG. 4B shows an experimentally obtained statistical distribution of a spectral power of the inter-beat intervals of 20 test individuals in rest state. The coefficient of symmetry of such a distribution is close to 2. The distribution is highly asymmetric. A logarithmic function to the base 10 has been applied to the values forming the statistical distribution shown in FIG. 4B. FIG. 4C shows the distribution of values thus standardized. The standardization function, in the present case the logarithmic function to the base 10, allows a symmetric distribution of standardized data to be obtained.

Figure 3B:
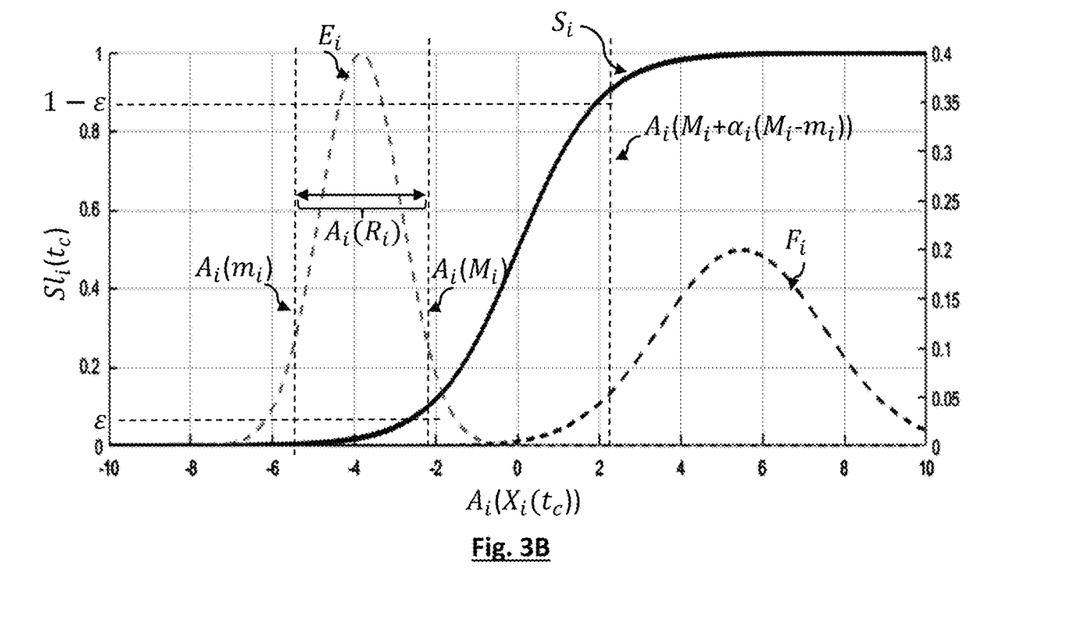
FIGS. 3B and 3C illustrate the case where the variation in the parameter with respect to the stress level is positive or negative, respectively.
Figure 3C:
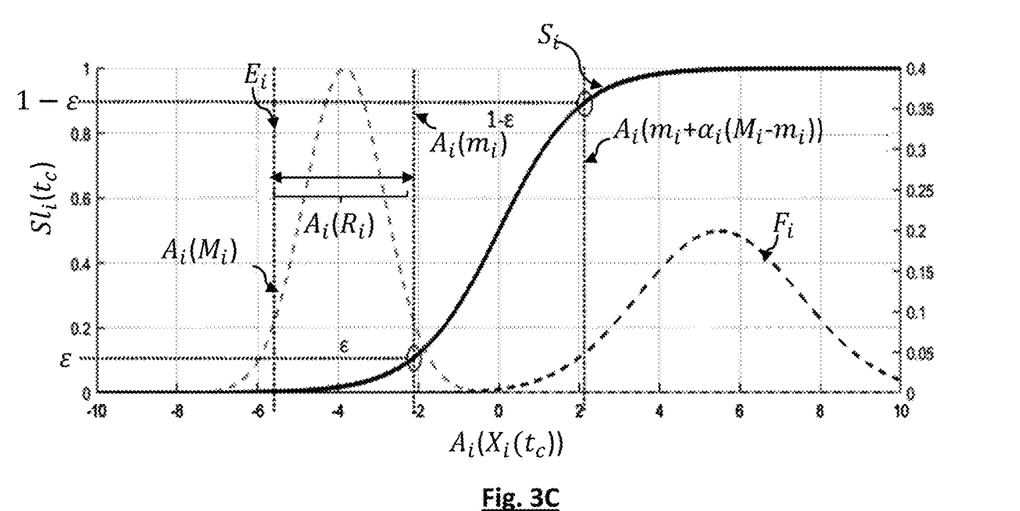

Following step 120, measured values, or measured then standardized values, the distribution of which is symmetric, are obtained. This facilitates implementation of step 130. Specifically, following the application of the standardization function, the data corresponding to the stress state are grouped, symmetrically, about a central value, the occurrence of which is maximal, as shown in FIGS. 3B and 3C.

Step 130: Determining a Normalization Function

The objective of the normalization function is to process the values such that the image, generated by the distribution function $S_i$, of the values processed by the normalization function $A_i$, leads to an optimal separation between the various states, and in particular between stressed states and unstressed states. This step assumes that the distribution function $S_i$ is known. As indicated above, the distribution function may be a sigmoid function. According to this example:

when, for the parameter $x_i$ in question, a standardization function $T_i$ was determined in step 120, the normalization function $A_i$ is applied to the standardized values, such that:

$$S_i(A_i(T_i(x_i(t_c)))) = \frac{1}{1 + e^{(A_i(T_i(x_i(t_c))))}} \quad (10)$$

when, for the parameter $x_i$ in question, a standardization function was not determined in step 120, the normalization function $A_i$ is applied to the measured values, such that:

$$S_i(A_i(x_i(t_c))) = \frac{1}{1 + e^{A_i(x_i(t_c))}} \quad (11)$$

In the rest of this example, the input variable processed by the normalization function $A_i$, which results from step 120, is designated by $X_i(t_c)$:

in the presence of standardization: $X_i(t_c) = T_i(x_i(t_c))$
without standardization: $X_i(t_c) = x_i(t_c)$.

FIG. 3B shows a distribution function $S_i$, which is applied to values $A_i(X_i(t_c))$, which are represented on the x-axis. The left y-axis corresponds to $S_i(A_i(X_i(t_c)))$, this, according to expression (4), corresponding to the computed stress index $Sl_i(t_c)$. In this step, the processed data are generated in the calibration phase. Thus, in each calibration period $t_c$, the stress index $Sl_i(t_c)$ is known. The example of FIG. 3B corresponds to a positive variation in the parameter with respect to the stress level: this means that a stressed state corresponds to an increase in the value of the parameter.

The form of the normalization function $A_i$ is predefined. The latter is parameterized by parameters $\theta_i$. Step 130 aims to determine the parameters $\theta_i$ of the normalization function $A_i$. In this example, the normalization function $A_i$ is a function $A_i(X_i) = a_i X_i + b_i$ (12) of affine type. The parameters of the function are $\theta_i = (a_i, b_i)$.

A first property of the normalization function $A_i$ is that the image, generated by the latter, of the input data $X_i(t_c)$, resulting from the calibration phase and corresponding to a rest state, and grouped in a rest interval $R_i$, form antecedents of a rest state $Sl_{i,rest}$ after the distribution function $S_i$ has been applied. Thus:

$$X_i(t_c) \in R_i \Leftrightarrow S_i(A_i(X_i(t_c))) \cong Sl_{i,rest} \quad (12')$$

The term $\cong$ signifies equal to a term to within an uncertainty $\varepsilon$. The uncertainty term c is defined beforehand.

The term $Sl_{i,rest}$ corresponds to the value of the stress indicator corresponding to a rest state. In the example shown in FIG. 3B, the distribution function $A_i$ is such that the stress indicator takes a minimum value $Sl_{i,rest}$ when the user is at rest, and a maximum value $Sl_{i,stress}$ when the user is in a stressed state. In the example shown in FIG. 3B, $Sl_{i,rest}=0$ and $Sl_{i,stress}=1$. Thus, expression (12) becomes:

$$X_i(t_c) \in R_i \Leftrightarrow S_i(A_i(X_i(t_c))) < \varepsilon \quad (13)$$

Alternatively, the variation with respect to stress is negative: this meaning that a stressed state corresponds to a decrease in the measured parameter. Such an alternative is shown in FIG. 3C.

The input data $X_{i,rest}(t_c)$, which correspond to a rest state, are comprised between a lower bound $m_i$ and an upper bound $M_i$, defining the interval $R_i$. During the normalization, the normalized values $A_i(X_i(t_c))$ are such that:

$$A_i(m_i) \leq A_i(X_{i,rest}(t_c)) < A_i(M_i) \quad (13')$$

Because the distribution of the input data $X_i(t_c)$ is considered to be symmetric, a lower limit $m_i$ and an upper limit $M_i$ may be defined such that:

$$m_i = \mu_i - \frac{z_i}{2}\sigma_i \text{ and } M_i = \mu_i + \frac{z_i}{2}\sigma_i$$

where $\mu_i$ and $\sigma_i$ are the mean and standard deviation of the distribution of the input data $X_{i,rest}(t_c)$ corresponding to the measurements taken, at rest, in the calibration phase, respectively. The parameter $z_i$ is a standardized amplitude. The amplitude $\Delta_i$ of the rest interval $R_i$ is equal to the product $\sigma_i z_i$. Thus, the rest interval $R_i$ is dependent on the parameter $z_i$, the value of $\sigma_i$ being obtained experimentally, from the input data $X_{i,rest}(t_c)$. The value of $z_i$ allows the rest interval $R_i$ and its amplitude $\Delta_i$, which is such that $\Delta_i = M_i - m_i$, to be determined.

In FIGS. 3B and 3C, the distribution $E_i$ formed by the normalized values $A_i(X_{i,rest}(t_c))$ has been illustrated (right y-axis). This distribution is bounded by $A_i(m_i)$ and by $A_i(M_i)$, which respectively correspond to the respective images of $m_i$ and $M_i$ generated by the normalization function $A_i$. These bounds define a reference interval $A_i(R_i)$, the latter corresponding to the image, generated by the function $A_i$, of the rest interval $R_i$.

A second property of the normalization function $A_i$ is that the image, generated by the latter, of the input data $X_i(t_c)$ resulting from the calibration phase and distant from the rest interval $R_i$ by a distance $d_i$ larger than or equal to $\alpha_i \Delta_i$, form antecedents of a stressed state $Sl_{i,stress}$, after the distribution function $S_i$ has been applied. The value $\beta_i \Delta_i$ is a threshold distance $d_i$. $\alpha_i$ is a positive parameter when the variation in the values of the parameter with respect to stress is positive (see FIG. 3B). $\alpha_i$ is a negative parameter when the variation in the values of the parameter with respect to stress is negative (see FIG. 3C).

Thus:

$$X_i(t_c) > M_i + \alpha_i \Delta_i \Leftrightarrow S_i(A_i(X_i(t_c))) \cong Sl_{i,stress} \quad (14)$$

Considering a positive variation with respect to stress, and a value $Sl_{i,stress}$ equal to 1, expression (14) becomes:

$$X_i(t_c) > M_i + \alpha_i \Delta_i \Leftrightarrow S_i(A_i(X_i(t_c))) > 1 - \varepsilon \quad (15)$$

The value of $\varepsilon$ is low with respect to 1. It may for example be equal to 0.1. In FIGS. 3B and 3C, the distribution $F_i$ formed by the normalized values $A_i(X_{i,stress}(t_c))$ has been illustrated. In FIG. 3B ($\alpha_i > 0$), the distribution $F_i$ is bounded by a bound the value of which is $A_i(M_i + \alpha_i \Delta_i)$, this corresponding to the image, generated by the function $A_i$, of $M_i + \alpha_i \Delta_i$. In FIG. 3C ($\alpha_i < 0$), the distribution $F_i$ is bounded by a bound the value of which is $A_i(m_i + \alpha_i \Delta_i)$, this corresponding to the image, generated by the function $A_i$, of $m_i + \alpha_i \Delta_i$.

The distribution function $S_i$ is for example of sigmoid type, such as defined with reference to the expressions (10) and (11). It may be deduced that:

$$A_i(M_i) = S_i^{-1}(\varepsilon) = \ln\left(\frac{\varepsilon}{1-\varepsilon}\right) \quad (16)$$

and $$A_i(M_i) + \alpha_i[A_i(M_i) - A_i(m_i)] = S_i^{-1}(1-\varepsilon) = S_i^{-1}(\varepsilon) = -A_i(M_i) \quad (17)$$

Assuming $A_i$ to be an affine transformation (see expression (12)), the following is obtained:

$$a_i = \frac{2\ln\left(\frac{1-\varepsilon}{\varepsilon}\right)}{\alpha_i(M_i - m_i)} \quad (18)$$

and $$b_i = \ln\left(\frac{\varepsilon}{1-\varepsilon}\right)\left[1 + 2\frac{M_i}{\alpha_i(M_i - m_i)}\right] \quad (19)$$

When the variation in the physiological parameter is negative between the rest state and the stressed state, as shown in FIG. 3C, then $\alpha_i < 0$, and it is possible to write:

$$A_i(m_i) = S_i^{-1}(\varepsilon) = \ln\left(\frac{\varepsilon}{1-\varepsilon}\right) \quad (20)$$

and $$A_i(m_i) + \alpha_i[A_i(m_i) - A_i(m_i)] = S_i^{-1}(1-\varepsilon) = S_i^{-1}(\varepsilon) = -A_i(m_i) \quad (21)$$

It then becomes:

$$a_i = \frac{2\ln\left(\frac{1-\varepsilon}{\varepsilon}\right)}{\alpha_i(M_i - m_i)} \quad (22)$$

and $$b_i = \ln\left(\frac{\varepsilon}{1-\varepsilon}\right)\left[1 + 2\frac{m_i}{\alpha_i(M_i - m_i)}\right] \quad (23)$$

The normalization function $A_i$ is dependent on the parameter $\alpha_i$ and on the parameter $z_i$.

The parameter $z_i$ is representative of the rest interval $R_i$, the image of which, generated by the distribution function $S_i$ composed with the normalization function $A_i$, corresponds to the rest level $Sl_{i,rest}$. More precisely, $z_i$ is representative of the width of the rest interval. The parameter $\alpha_i$ dimensions the threshold distance $d_i$, between the rest interval and a stressed interval, the image of which, generated by the distribution function $S_i$ composed with the normalization function $A_i$, is equal to $Sl_{i,stress}$ to within the uncertainty term $\varepsilon$.

Figure 3D:
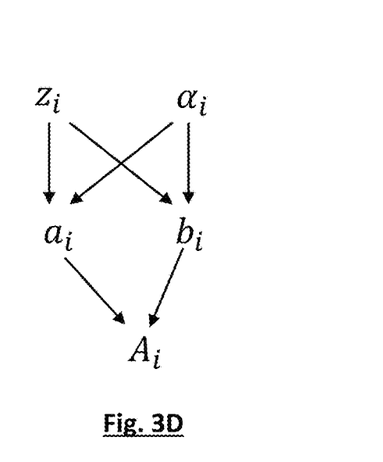
FIG. 3D illustrates a hierarchy between parameters defining a normalization function.

The optimization of the parameters $z_i$ and $\alpha_i$ is carried out successively, starting with the optimization of the parameter $z_i$. It is performed using the fact that, in the calibration phase, in each calibration period $t_c$, each state $Sl_i(t_c)$ of the test individual is known. The optimization consists in setting one parameter (for example $z_i$), and making the other parameter (for example $\alpha_i$) vary while analyzing the classification performance given by the distribution function $f_i((X_i(t_c)) = S_i \circ A_i(X_i(t_c))$. The normalization function $A_i$ is parameterized by the parameters $a_i$ and $b_i$ such as defined by expressions (22) and (23), the latter themselves being dependent on the parameters $\alpha_i$ and $z_i$, the latter having a hyperparameter function. FIG. 3D illustrates the hierarchical structure of the dependency between $z_i$ and $\alpha_i$ on the one hand and $a_i$ and $b_i$ on the other hand. The optimization of the parameters $z_i$ and $\alpha_i$ allows optimized parameters $z_{i,opt}$ and $\alpha_{i,opt}$ to be obtained. The latter are used to define the parameters $a_i$ and $b_i$ of the normalization function $A_i$.

By classification performance, what is for example meant is sensitivity, which corresponds to 1—the rate of false negatives, and specificity, which corresponds to 1 minus the rate of false positives. Other statistical indicators, for example a "Cohen's d" test, which is known to those skilled in the art, may also be employed. Cohen's d corresponds to an inter-class distance, in the present case a distance between the distributions of the values respectively considered to be representative of a stressed state and of an unstressed state. The unstressed state is a rest state or an intermediate state.

For example, if two statistical distributions are considered that have mean, standard-deviation and population values denoted $\mu_1$, $\sigma_1$, $n_1$ and $\mu_2$, $\sigma_2$ and $n_2$, respectively, the Cohen's d may be such that:

$$d = \frac{\mu_1 - \mu_2}{\sqrt{\frac{(\mu_1 - 1)s_1^2 + (\mu_2 - 1)s_2^2}{n_1 + n_2 - 2}}}$$

The inventors have established a classification-performance indicator c, such that:

$c = \rho d$ where:

$\rho$ is a likelihood ratio, such that $$\rho = \frac{1-\beta}{\gamma}$$

where $\beta$ and $\gamma$ designate sensitivity and specificity, respectively;

d corresponds to the aforementioned Cohen's d.

In order to determine the parameter $z_i$ that is optimal in terms of classification performance, the parameter $\alpha_i$ is set to an absolute value equal to 0.01. Next, $z_i$ is varied in increments of 0.25 between two predefined bounds, between 1 and 5 for example. The optimal value of $z_i$, denoted $z_{i,opt}$, is such that:

$$z_{i,opt} = \underset{z_i}{\mathrm{argmax}}(c_{\alpha_i \approx 0}) \quad (25)$$

The notation $c_{\alpha_i \approx 0}$ corresponds to the fact that the performance indicator is computed considering $\alpha_i$ to be close to 0, and for example equal to 0.01 (when $\alpha_i > 0$) or −0.01 (when $\alpha_i < 0$). During the determination of $z_{i,opt}$, classification performance is determined on the basis of two classes: the rest state and the "non-rest" state, the latter containing the intermediate states and the stressed state. It is a question of evaluating the ability of the distribution function to correctly classify the rest state.

After $z_{i,opt}$ has been determined, the optimal parameter $\alpha_i$ is determined setting the parameter $z_i$ such that $z_i = z_{i,opt}$. Next, $\alpha_i$ is varied in increments of 0.1 between two predefined bounds, between 0 and 3 for example when $\alpha_i > 0$ or between −3 and 0 when $\alpha_i < 0$. The optimal value of $\alpha_i$, which is denoted $\alpha_{i,opt}$, is such that:

$$\alpha_{i,opt} = \underset{\alpha_i}{\mathrm{argmax}}\left(c_{z_i = z_{i,opt}}\right) \quad (26)$$

The notation $c_{z_i = z_{i,opt}}$ corresponds to the fact that the performance indicator is computed considering $z_i = z_{i,opt}$. During the determination of $\alpha_{i,opt}$, classification performance is determined on the basis of two classes: the stressed state and the "unstressed" state, the latter containing the intermediate states and the rest state. It is a question of evaluating the ability of the distribution function to correctly classify the stressed state.

Figure 5A:
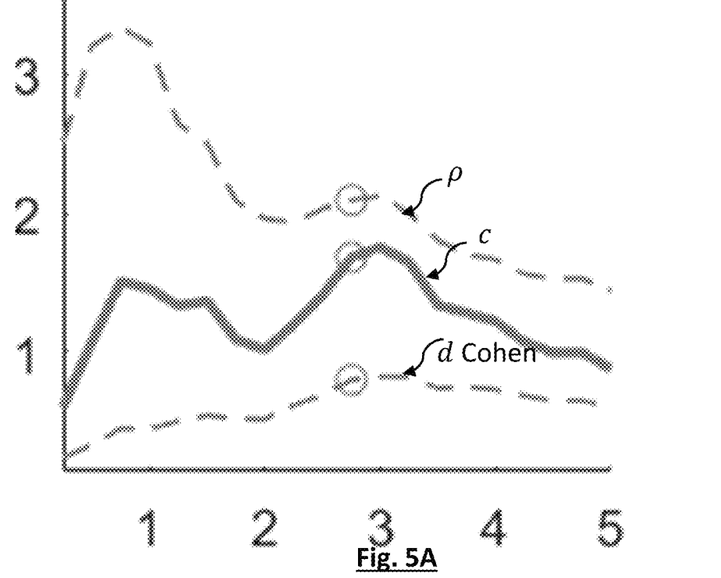
FIGS. 5A and 5B show optimization of the extent of the rest interval and optimization of a scale factor, respectively.
Figure 5B:
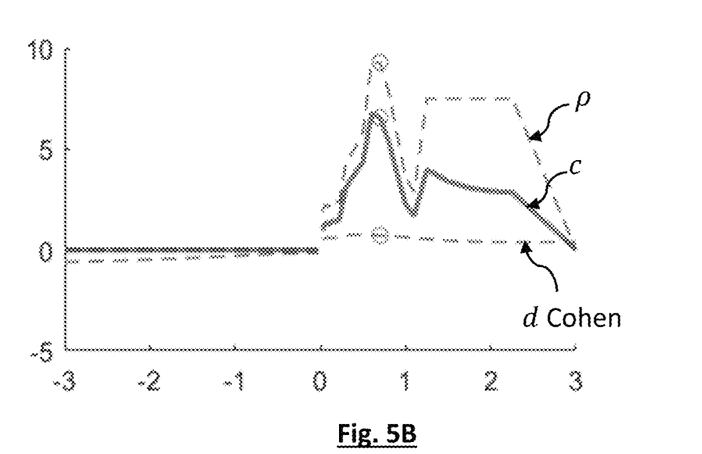

FIG. 5A illustrates a variation, as a function of $z_i$ (x-axis) of the likelihood ratio ρ, of Cohen's d and of the classification-performance indicator c. In this example, the studied parameter was the variance of heart rate. FIG. 5B illustrates a variation, as a function of $\alpha_i$ (x-axis) of the likelihood ratio ρ, of Cohen's d and of the classification-performance indicator c. In this example, the studied parameter was also the variance of heart rate. FIGS. 5A and 5B illustrate the ability to determine $z_{i,opt}$ and $\alpha_{i,opt}$, respectively.

According to one variant, the parameters $\alpha_{i,opt}$ and $z_{i,opt}$ may be determined simultaneously. According to another variant, $\alpha_{i,opt}$ may be determined before $z_{i,opt}$.

The determination of $z_{i,opt}$ and $\alpha_{i,opt}$ described above corresponds to one example, based on a determination of specificity, sensitivity and Cohen's d. More generally, the parameters $z_{i,opt}$ and $\alpha_{i,opt}$ may be determined on the basis of classification performance determined in a training phase, in which the state of each test individual is known.

Figure 6A:
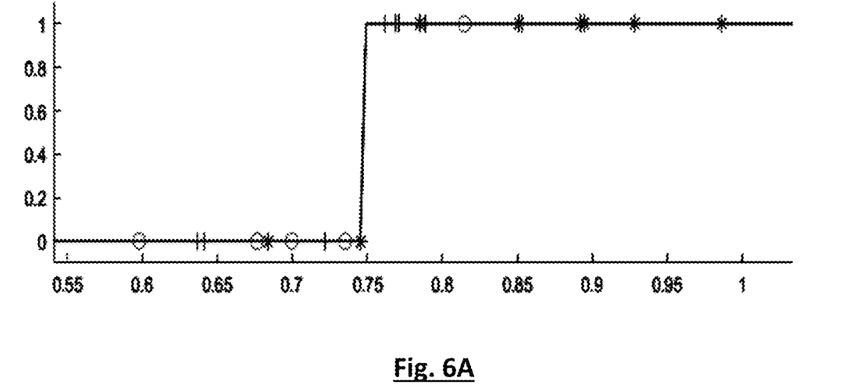
FIG. 6A shows application of the membership function taking into account a scale factor of zero.
Figure 6B:
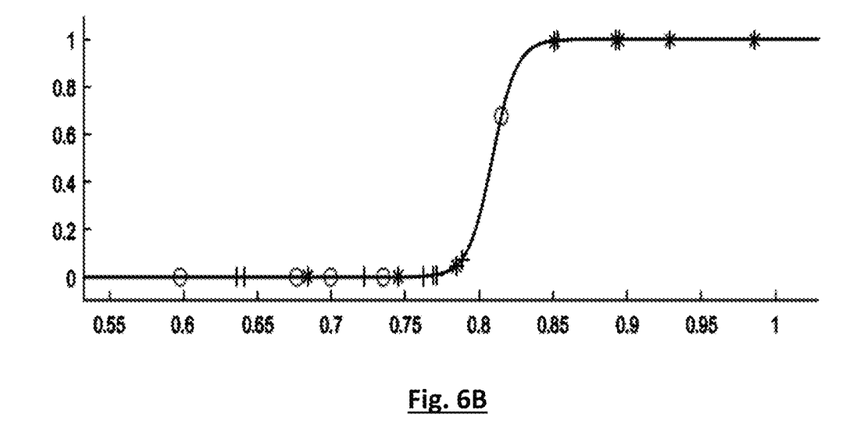
FIG. 6B shows application of the membership function taking into account a scale factor that has been subject to an optimization.

FIG. 6A shows a distribution function $S_i$ composed with a normalization function $A_i$ established with $z_i = z_{i,opt}$ and $\alpha_i = 0$. FIG. 6B shows a distribution function $S_i$ composed with a normalization function $A_i$ established with $z_i = z_{i,opt}$ and $\alpha_i = \alpha_{i,opt}$. In FIGS. 6A and 6B, the parameters established while the test individual is in a rest state, stressed state and an intermediate state are identified by circles O, crosses + and stars *, respectively. In FIG. 6A, classification errors may be seen (for example false positives: circles O the y-coordinate of which corresponds to a stress level $Sl_i$ corresponding to the stressed state). This curve also returns false negatives: stars * the y-coordinate of which corresponds to a stress level $Sl_i$ corresponding to the rest state. FIG. 6B contains fewer classification errors.

Following step 130, the normalization function $A_i$ corresponding to the physiological parameter $x_i$, is obtained.

Step 140: Determining the Membership Function $f_i$

In step 140, the membership function is determined according to expressions (4) or (5), using:
the optional standardization function $T_i$ resulting from step 120;
the distribution function $S_i$ taken into account in step 130;
the normalization function $A_i$ defined following step 130.

Steps 100 to 140 may be respectively implemented for various physiological parameters $x_i$. As many distribution functions are obtained as there are physiological parameters in question. As indicated above, the distribution functions may be combined, in particular in the form of a weighted summation, so as to establish a stress level.

Figure 7:
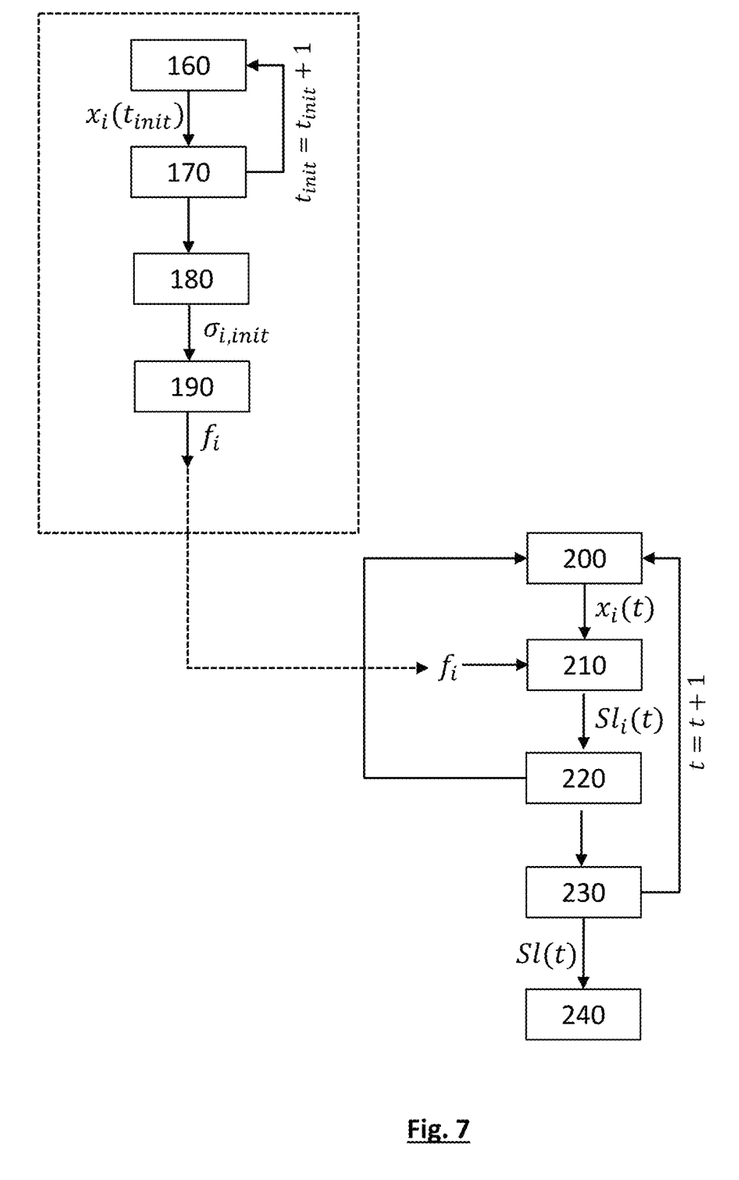
FIG. 7 shows the steps of a method for determining a stress level of a user, using at least one membership function such as determined in the steps schematically shown in FIG. 3A.

FIG. 7 shows the main steps of implementation of a method for determining a stressed state, by implementing a membership function as determined following step 140.

In step 200, one or more physiological parameters $x_i(t)$ are measured in a measurement period t. Each physiological parameter $x_i$ measured in each measurement period corresponds to one physiological parameter addressed during the calibration.

In step 210, the membership function $f_i$, which is defined beforehand for each physiological parameter, is applied to the value $x_i(t)$ of the physiological parameter in the measurement period, so as to determine a stress level $Sl_i(t) = f_i(x_i(t))$ relating to the physiological parameter $x_i$.

In step 220, the stress level $Sl(t)$ of the user, during the measurement period t, is determined depending on each stress level $Sl_i(t)$ established, for each addressed physiological parameter, during step 210.

In step 230, the method is reiterated for another measurement period or it is decided to exit the algorithm.

According to one variant, forming the subject matter of steps 160 to 190, the method comprises an initialization phase, in which the user is exclusively in a rest state, or considered in a rest state. The initialization consists in taking measurements of at least one physiological parameter $x_i(t_{init})$, so as to estimate a range of variation. The measurements are taken in various initialization periods $t_{init}$. A dispersion indicator is determined, characterizing the range of variation of the parameter $x_i$ during the various initialization periods $t_{init}$. The dispersion indicator may for example be a standard deviation $\sigma_{i,init}$.

The dispersion indicator $\sigma_{i,init}$ thus determined is used to determine the bounds $M_i$ and $m_i$ of the rest interval on the basis of $z_i$. The following expressions are then used:

$$m_i = \mu_i - \frac{z_{i,opt}}{2}\sigma_{i,init} \quad (27)$$

and $$M_i = \mu_i + \frac{z_{i,opt}}{2}\sigma_{i,init} \quad (28)$$

Thus, according to this variant, the initialization is performed only with values of the parameter that are measured during the calibration, while the user is considered to be in a rest state. The initialization does not require measurements of a physiological parameter to be taken while the user is in a stressed state. One advantage of the method is that the initialization is faster and simpler to carry out. Another advantage is that the initialization may be repeated periodically, in order to take into account potential physiological user variability. Since the initialization is simple to carry out, it may be repeated frequently.

Steps 160 to 190 are then as follows:
Step 160: taking an initialization measurement $x_i(t_{init})$
Step 170: reiterating step 160 or passing to step 180
Step 180: computing the dispersion indicator $\sigma_{i,init}$
Step 190: using the dispersion indicator $\sigma_{i,init}$ to adjust the membership function $f_i$ used in step 210, by combining expressions (27) and (28) with expressions (18) and (19) or (22) and (23).

According to another variant, the initialization is not performed and the membership function, relating to one parameter, or even to each parameter in question, is established without adjustment of the membership function resulting from the calibration.

The invention will possibly be employed to track the stress level of users. It may for example be a question of tracking stress level in a professional environment, or of tracking stress level of users subject to anxiety in particular situations, in a means of transportation for example. It may also be applied to track the stress level of a sportsperson. Thus, the stress level can be a level of anxiety or effort, whether physical or mental, or a level of excitement. The stress level can correspond to a mental load of the user: joy, anger, anxiety, fatigue, feeling of lack. The invention can also be applied to the determination of a level of wakefulness or sleepiness.

The invention claimed is:

1. A method for determining a membership function, the membership function allowing a stress level of a user to be determined on the basis of a physiological parameter measured on the user, during a measurement period, using a sensor, the membership function varying, depending on the physiological parameter, between:
   a first value, representative of a rest state; and
   a second value, representative of a stressed state;
   the membership function taking into account a distribution function, which is defined beforehand, the distribution function being a continuous and monotonic function, the distribution function being applied to a normalized parameter that is established on the basis of a measured physiological parameter, the method comprising:
   a) measuring values of a physiological parameter with the sensor in various calibration periods on at least one test individual, each test individual being placed, in each calibration period, either in a rest state or in a stressed state, or in an intermediate state, the intermediate state being a state in which the test individual is considered to be neither in a stressed state, nor in a rest state;
   b) on the basis:
      of the values of the physiological parameter resulting from a); and
      of the distribution function;
   determining, using processing circuitry, a normalization function, the normalization function being configured to be applied to the values of the physiological parameter resulting from a), in order to establish normalized values, the determination of the normalization function comprising:
   an optimization of a rest interval, representative of the values of the parameters measured when each test individual is at rest; and
   an optimization of a threshold distance, between the rest interval, and a stressed interval, representative of the values of the parameter measured when each test individual is in a stressed state; and
   c) determining, using the processing circuitry, the membership function associated with the physiological parameter, the membership function comprising a composition of the distribution function and the normalization function.

2. The method of claim 1, wherein, in a), the values of the physiological parameter that are measured while each test individual is in a stressed, rest or intermediate state are grouped into a stressed class, a rest class and an intermediate class, respectively, and wherein, in step b),
   the rest interval is optimized so as to optimize a classification, by the distribution function, of normalized values corresponding to the rest class and to a union of the intermediate class and of the stressed class, respectively; and
   the threshold distance is optimized so as to optimize a classification, by the distribution function of normalized values corresponding to the stressed class and to a union of the intermediate class and of the rest class, respectively.

3. The method of claim 2, wherein b) comprises determining:
   an indicator of classification of the normalized values between the rest class and a union of the intermediate class and of the stressed class, the classification indicator being based on a proportion of false positives and of false negatives; and
   an indicator of classification of the normalized values between the stressed class and a union of the intermediate class and of the rest class, the classification indicator being based on a proportion of false positives and of false negatives.

4. The method of claim 1, wherein b) comprises:
   determining an optimal rest interval, by setting the threshold distance; then
   determining the optimal threshold distance, depending on the optimal rest interval.

5. The method of claim 4, wherein b) comprises optimizing an extent of the rest interval.

6. The method of claim 5, wherein b) comprises optimizing a scale factor, the threshold distance being determined by multiplying the scale factor by the extent of the rest interval.

7. The method of claim 1, wherein the normalization function is an affine function, and wherein b) comprises determining parameters of the affine function on the basis of the optimized rest interval and of the optimized threshold distance.

8. The method of claim 1, wherein
   a) comprises applying a standardization function to the values of the physiological parameter measured at rest, to obtain standardized values of said physiological parameter, the standardization function being concave, and
   b) comprises determining, using the processing circuitry, the normalization function, the normalization function being determined on a basis:
      of the standardized values of the physiological parameter resulting from a), and
      of the distribution function;
   wherein the normalization function is configured to be applied to the standardized values of the physiological parameter resulting from a); and in c), the membership function comprises a composition of the distribution function, the normalization function, and the standardization function.

9. The method of claim 1, wherein:
steps a) to c) form a sequence of steps that is associated with the physiological parameter measured in a), and leading to the determination of a membership function associated with the physiological parameter;
the method further comprises various sequences of steps a) to c), respectively associated with various physiological parameters, so as to determine various membership functions, each membership function being respectively associated with one physiological parameter.

10. The method of claim 8, wherein the standardization function is of logarithmic or square-root type.

11. The method of claim 8, wherein a) comprises, using the processing circuitry:
computing a coefficient of asymmetry of a distribution of the values of the physiological parameter that are measured when each test individual is at rest, the coefficient of asymmetry quantifying the asymmetry of the distribution;
comparing the coefficient of asymmetry to a predefined threshold; and
depending on the comparison, applying the standardization function to the values measured at rest to obtain standardized values of the physiological parameter.

12. A method for determining a stress level of a user, depending on a physiological parameter measured on the user, during a measurement period, the value of which is liable to vary depending on the stress level of the user, the method comprising:
i) measuring a value of the physiological parameter during a measurement period;
ii) applying a membership function to the value of the physiological parameter measured in step i); and
iii) estimating the stress level of the user depending on the value of the membership function computed in step ii);
wherein the membership function is a function determined using the method of claim 1.

13. The method of claim 12, comprising an initialization phase, containing various initialization periods, in which periods the user is considered to be in a rest state, the initialization phase comprising:
measuring, in each initialization period, one physiological parameter; and
determining an indicator of dispersion of the values measured in each initialization period;
the method comprising, prior to steps i) to iii), adjusting the membership function established for the physiological parameter so as to take into account the dispersion indicator.

14. A device, comprising the sensor, configured to be placed against a body of an individual, the sensor being configured to measure a physiological parameter of the individual, the device further comprising the processing circuitry, configured to receive measurements from the sensor and estimate a stress level of the individual according to the method of claim 12.

15. A method for determining a stress level of a user, depending on a plurality of physiological parameters of the user, the value of each physiological parameter being liable to vary depending on the stress level of the user, the method comprising:
i) measuring values of various physiological parameters during a measurement period;
ii) for each value of the physiological parameter measured in i), applying a membership function associated with the physiological parameter; and
iii) estimating the stress level by combining the values of the membership functions computed in step i);
wherein at least one membership function, associated with one physiological parameter, is a function determined using the method of claim 1.

16. The method of claim 15, comprising an initialization phase, containing various initialization periods, in which periods the user is considered to be in a rest state, the initialization phase comprising:
measuring, in each initialization period, one physiological parameter; and
determining an indicator of dispersion of the values measured in each initialization period;
the method comprising, prior to steps i) to iii), adjusting the membership function established for the physiological parameter so as to take into account the dispersion indicator.

17. A device for determining a stress level of a user, the device comprising a sensor, configured to be placed against a body of an individual, the sensor being configured to measure a value of a physiological parameter of the individual during a measurement period, the device further comprising processing circuitry, configured to
apply a membership function to the value of the physiological parameter measured by the sensor during the measurement period; and
estimate the stress level of the user depending on the value of the membership function,
wherein the membership function is determined using the method of claim 8.

\* \* \* \* \*